US009302978B1

(12) United States Patent
Mairata et al.

(10) Patent No.: US 9,302,978 B1
(45) Date of Patent: Apr. 5, 2016

(54) PROCESS FOR THE PREPARATION OF NITROBENZENE BY ADIABATIC NITRATION

(71) Applicant: Covestro Deutschland AG, Leverkusen (DE)

(72) Inventors: Antoni Mairata, Dusseldorf (DE); Thomas Knauf, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/785,763

(22) PCT Filed: Apr. 24, 2014

(86) PCT No.: PCT/EP2014/058345
§ 371 (c)(1),
(2) Date: Oct. 20, 2015

(87) PCT Pub. No.: WO2014/177450
PCT Pub. Date: Nov. 6, 2014

(30) Foreign Application Priority Data

Apr. 29, 2013 (EP) .................................. 13165822

(51) Int. Cl.
*C07C 205/00* (2006.01)
*C07C 201/08* (2006.01)
*C07C 201/16* (2006.01)

(52) U.S. Cl.
CPC ............. *C07C 201/08* (2013.01); *C07C 201/16* (2013.01)

(58) Field of Classification Search
CPC ..... C07C 201/08; C07C 205/06; C07C 201/16
USPC ........................................................ 568/939
See application file for complete search history.

(56) References Cited

U.S. PATENT DOCUMENTS

| 2,256,999 | A | 9/1941 | Bert |
| 5,313,009 | A | 5/1994 | Guenkel et al. |
| 5,616,818 | A | 4/1997 | Pirkl et al. |
| 5,763,697 | A | 6/1998 | Hermann et al. |
| 6,288,289 | B1 | 9/2001 | Boyd et al. |
| 6,562,247 | B2 | 5/2003 | Gillis et al. |
| 7,344,650 | B2 | 3/2008 | Knauf et al. |
| 7,763,759 | B2 | 7/2010 | Knauf et al. |
| 7,781,624 | B2 | 8/2010 | Rausch et al. |
| 8,357,827 | B2 | 1/2013 | Muenning et al. |
| 2003/0055300 | A1 | 3/2003 | Chrisochouu et al. |
| 2013/0204043 | A1 | 8/2013 | Knauf et al. |

FOREIGN PATENT DOCUMENTS

DE 3409117 9/1985

*Primary Examiner* — Jafar Parsa
(74) *Attorney, Agent, or Firm* — Donald R. Palladino

(57) ABSTRACT

The present invention relates to a continuously operated adiabatic process for the preparation of nitrobenzene by nitration of benzene with nitric acid and sulfuric acid, in which the dilute sulfuric acid obtained after the nitration has taken place and the crude nitrobenzene has been separated off from the aqueous phase is concentrated for the purpose of re-use in the nitration, and after its concentration, at least one minute before it comes into contact with fresh nitric acid again an oxidizing agent is added such that a concentration of the oxidizing agent of from 10 ppm to 5,000 ppm, based on the total weight of the concentrated sulfuric acid to be recycled into the nitration, is established.

7 Claims, No Drawings

PROCESS FOR THE PREPARATION OF NITROBENZENE BY ADIABATIC NITRATION

CROSS-REFERENCE TO RELATED APPLICATIONS

This Application is a National Phase Application of PCT/EP2014/058345, filed Apr. 24, 2014, which claims priority to European Application No.: 13165822.1, filed Apr. 29, 2013, each of which being incorporated herein by reference.

FIELD

The present invention relates to a continuously operated adiabatic process for the preparation of nitrobenzene by nitration of benzene with nitric acid and sulfuric acid, in which the dilute sulfuric acid, obtained after the nitration has taken place and the crude nitrobenzene has been separated off from the aqueous phase, is concentrated for the purpose of re-use in the nitration, and after its concentration, at least one minute before it comes into contact with fresh nitric acid again an oxidizing agent is added such that a concentration of the oxidizing agent of from 10 ppm to 5,000 ppm, based on the total weight of the concentrated sulfuric acid to be recycled into the nitration, is established.

BACKGROUND

Nitrobenzene is an important intermediate product of the chemical industry which is required in particular for the preparation of aniline and therefore also for the preparation of di- and polyisocyanates of the diphenylmethane series and the polyurethanes based thereon.

The nitration of benzene with nitric acid to give a crude nitrobenzene has already been the subject of numerous publications and patent applications. The present current processes substantially correspond to the concept of adiabatic nitration of benzene by a mixture of sulfuric and nitric acid (so-called mixed acid). Such a process was claimed for the first time in U.S. Pat. No. 2,256,999 and is described in present-day embodiments, for example, in EP 0 436 443 B1, EP 0 771 783 B1 and U.S. Pat. No. 6,562,247 B2. The processes with an adiabatic reaction procedure are distinguished in particular in that no technical measures are taken to supply heat to or remove heat from the reaction mixture. The starting substances benzene and nitric acid are reacted in a large excess of sulfuric acid, which takes up the heat of reaction liberated and the water formed during the reaction.

The reaction procedure is in general such that the nitric acid and sulfuric acid are combined to form so-called nitrating acid (also called mixed acid). Benzene is metered into this nitrating acid. The reaction products are substantially water and nitrobenzene. Benzene is employed in the nitration reaction at least in the stoichiometric amount, based on the molar amount of nitric acid, but preferably in a 2% to 10% excess. The reaction mixture which is obtained after the reaction zone and is substantially free from nitric acid is fed to a phase separation apparatus in which two phases are formed, the first being called crude nitrobenzene and substantially comprising nitrobenzene, benzene and a quantity of sulfuric acid and water which is dissolved in the nitrobenzene, and the second, called circulating acid, substantially comprising water, sulfuric acid and nitrobenzene dissolved in the sulfuric acid. The circulating acid separated off in the phase separation apparatus is, as described in U.S. Pat. No. 5,313,009, introduced into an apparatus for flash evaporation of the water, in which, by application of a reduced pressure and utilizing the high temperature of the circulating acid which has been achieved by the adiabatic procedure, water is evaporated out of the circulating acid, so that a concentrated sulfuric acid is obtained, the concentration of which substantially corresponds to the concentration before the reaction zone. After the concentration of the sulfuric acid, the sulfuric acid obtained in this way is fed into the reaction without further treatment.

The quality of an adiabatic process for the nitration of aromatic hydrocarbons is defined on the one hand by the content in the product of undesirable by-products of the reaction which are formed by multiple nitration or oxidation of the aromatic hydrocarbon or of the nitroaromatic. The aim in the preparation of nitrobenzene is to minimize the content of dinitrobenzene and of nitrophenols, in particular of trinitrophenol (picric acid), which is to be classified as explosive. On the other hand, the quality of an adiabatic process is defined as it being possible to prepare nitrobenzene without loss of industrial production.

By recycling the sulfuric acid, a sulfuric acid circulation is formed, which comprises the reaction zone, phase separation apparatus, evaporator, buffer tank and connecting lines. It is reported in EP 2 070 907 A1 that metal ions which form sparingly soluble metal sulfates together with sulfate in the sulfuric acid may be present in the sulfuric acid. These metals include the elements Al, Ca, Cr, Mn, Fe, Co, Ni, Cu, Sr, Cd and Ba, in particular Ca and Fe. If the concentration of these metal ions which form sparingly soluble metal sulfates exceeds the solubility limit, metal sulfates precipitate out in the sulfuric acid in the form of a solid and are carried along in the circulation with the sulfuric acid as solids, until they settle and accumulate on a surface or at a narrow point.

It is likewise a known phenomenon that the solubility limit of the metal ions which form sparingly soluble metal sulfates depends greatly on the temperature of the solution, that is to say the temperature of the sulfuric acid. Thus, metal ions dissolve less in cold sulfuric acid than in hot, and consequently metal sulfates are particularly easily produced as a solid in cold sulfuric acid or at points where sulfuric acid is cooled, such as is the case e.g. in heat exchangers. This production of solids in heat exchangers is to be regarded as problematic, since it leads to a covering of the surface of the heat exchanger and therefore to a deterioration in the heat transfer coefficient, and also limits the possible amount flowing through this due to the reduction in the free cross-section of the lines in the heat exchanger.

EP 2 070 907 A1 thus discloses that a cleaning of heat exchangers and lines carrying sulfuric acid to remove solid metal sulfates which have precipitated out is no longer necessary if in the nitration of benzene by a mixed acid containing sulfuric and nitric acid the sulfuric acid obtained again by flash evaporation of water is not recycled completely into the reaction zone as circulating acid, but is partly purged out and replaced by fresh sulfuric acid of low metal ion content.

Periodic flushing of the apparatuses, such as e.g. all those heat exchangers which carry the circulating acid, in order to remove the crystallized metal sulfates from the concentrated sulfuric acid (DE 340 91 17 C2) can thus be dispensed with.

In contrast to the solution disclosed in EP 2 070 907 A1 for avoiding precipitates in heat exchangers and pipelines of a nitration plant, in continuous operation of a nitration plant such as is described in EP 2 070 907 A1 black carbon-containing precipitates which settle in the phase separation apparatus for the crude product, in the crude nitrobenzene condenser and in the neighbouring pipelines have been found.

There was therefore a need for a further improvement in the process for the preparation of nitrobenzene. In particular a smooth operation of the continuous, adiabatic nitration of benzene should be ensured, i.e. in particular the formation of troublesome precipitates, which in the extreme case can lead to the continuous process having to be shut down for cleaning purposes, should be avoided.

SUMMARY

Taking into account this need, the present invention provides a continuously operated adiabatic process for the preparation of nitrobenzene by nitration of benzene, in which
a) a benzene-containing stream (a.1) is reacted in a reactor with sulfuric acid (a.2) and nitric acid (a.3) under adiabatic conditions, wherein benzene is employed in a stoichiometric excess, based on nitric acid (a.3), of from preferably 2.0% to 20%, particularly preferably from 5.0% to 10% of theory,
b) the process product obtained in step a) is separated in a phase separation apparatus into an aqueous phase (b.1) comprising sulfuric acid and an organic phase (b.2) comprising nitrobenzene,
c) the aqueous phase (b.1) obtained in step b) is concentrated by evaporation of water to give an aqueous phase (c.1) having an increased sulfuric acid concentration compared with (b.1), wherein phase (c.1) is returned into step a) and is employed as a component of (a.2),
d) the organic phase (b.2) obtained in step b) is worked up to give pure nitrobenzene (d.1), preferably by washing with aqueous media and subsequent rectification, wherein excess benzene, which is reused in the nitration as so-called recycled benzene, and water are separated off from the end product,
wherein
an oxidizing agent (c.2), preferably nitric acid (c.2.1), nitrous acid (c.2.2) and/or nitrosylsulfonic acid (c.2.3), is added to the concentrated aqueous phase (c.1) comprising sulfuric acid at least 1 minute, preferably 1 minute to 10 minutes, particularly preferably 3 minutes to 7 minutes before the phase (c.1) comes into contact with the nitric acid stream (a.3), to an extent such that a concentration of oxidizing agent (c.2) of from 10 ppm to 5,000 ppm, preferably 50 ppm to 2,000 ppm and particularly preferably 100 ppm to 1,000 ppm, in each case based on the total weight of the concentrated aqueous phase (c.1) comprising sulfuric acid to be returned into step a), is established.

DETAILED DESCRIPTION

Surprisingly, it has in fact been found that the addition of small amounts of an oxidizing agent, preferably nitric acid (c.2.1), nitrous acid (c.2.2) and/or nitrosylsulfonic acid (c.2.3), to the circulating sulfuric acid during the recycling to the reaction reduces to completely prevents the formation of the abovementioned precipitates.

The excess of benzene, based on nitric acid, of from 2.0% to 20%, preferably from 5.0% to 10% of theory relates to the molar ratio of benzene and nitric acid.

Theoretically, one mole of nitric acid reacts with one mole of benzene to give one mole of nitrobenzene.

The abovementioned concentrations of oxidizing agent (c.2) In ppm relate to the pure oxidizing agent, in the case of, for example, nitric acid (c.2.1) that is to say to hypothetical pure $HNO_3$ and not to the aqueous solution. If necessary, the oxidizing agent (c.2) can also be generated in situ; for example by addition of sodium nitrite to the phase (c.1) comprising sulfuric acid (formation of nitrous acid (c.2.2)). In these cases also the concentration of oxidizing agent (c.2) in ppm relates to the pure oxidizing agent, that is to say, in the example mentioned to hypothetically pure $HNO_2$.

The individual steps of the invention are explained in detail below. In this context, various embodiments can be combined with one another as desired, as long as the opposite does not clearly emerge from the context for the person skilled in the art.

Step a) can in principle be carried out by all the adiabatic nitration processes known from the state of the art. A tube reactor in which several dispersing elements are arranged in distribution over the length of the reactor and ensure intensive dispersing and thorough mixing of benzene, nitric acid and sulfuric acid is preferably employed for carrying out this step of the process according to the invention. Such a reactor and the form of dispersing elements which can be employed are described, for example, in EP 0 708 076 B1 (FIG. 2) and EP 1 291 078 A2 (FIG. 1). Preferably, step a) is carried out in process procedure such as is described in DE 10 2008 048 713 A1, in particular paragraph [0024]. Preferably, in this context first the nitric acid (a.3) and then the benzene (a.1) are metered into the sulfuric acid (a.2). The residence time between the addition of nitric acid into the circulating sulfuric acid and the addition of benzene into the nitrating acid mixture at the entry of the nitration reactor is a few seconds.

The phase separation in step b) is likewise carried out in a separating tank known to the person skilled in the art by processes known per se from the state of the art. The aqueous phase (b.1) substantially comprises (as a result of the formation of water of reaction and due to the entraining of water into the reaction from the nitric acid employed) dilute sulfuric acid together with inorganic impurities, and the organic phase (b.2) substantially comprises nitrobenzene together with excess benzene and organic impurities.

The concentration of the aqueous phase (b.1) in step c) is in principle carried out as known from the state of the art. The sulfuric acid in the aqueous phase is concentrated in an expansion evaporator (also called flash evaporator), by evaporating water into a region of reduced pressure. With the correct choice of the reaction conditions in the adiabatic nitration of benzene with mixed acid, such a high heating of the aqueous phase (b.1) comprising sulfuric acid is achieved with the heat of reaction of the exothermic reaction that the concentration and temperature of the aqueous phase comprising sulfuric acid which this had before the reaction with benzene and nitric acid on entry into the reaction space can simultaneously be established again in the expansion evaporator, i.e. (c.1) corresponds to (a.2) with respect to temperature and concentration. This is described in EP 2 354 117 A1, in particular paragraph [0045].

The work-up of the organic phase (b.2) in step d) is in principle carried out as known from the state of the art. A preferred procedure is described below:

The organic phase (b.2), which generally still comprises traces of acid, is washed in one to two washes, preferably one wash, with an aqueous wash liquid and is then separated from the acid aqueous phase by phase separation; in the case of several washes after each individual wash (step d(i)). In this operation the acid residues which the crude nitrobenzene (b.2) contains are washed out; this process step is therefore also called acid wash. This step is adequately known from the state of the art and is therefore only briefly outlined here. Preferably, aqueous streams obtained during operation are recycled for carrying out this acid wash.

The organic phase obtained in this way is then washed in one to two, preferably one alkaline wash(es) with an aqueous solution of a base, preferably chosen from sodium hydroxide, sodium carbonate or sodium bicarbonate, and is then separated from the alkaline wash water by phase separation; in the case of several washes after each individual wash (step d(ii)). Sodium hydroxide solution is particularly preferably employed as the aqueous base solution. This step is adequately known from the state of the art and is therefore only briefly outlined here. The pH of the sodium hydroxide solution employed and its weight ratio to the organic phase are established such that acid impurities (e.g. nitrophenols formed as by-products and acid residues which have not been completely removed in step d(i)), are largely to completely, preferably completely neutralized in the alkaline wash. The subsequent working up of the alkaline waste water can be carried out by the processes of the state of the art, e.g. in accordance with EP 1 593 654 A1 and EP 1 132 347 A2.

The organic phase obtained in this way is finally washed with water in at least one, preferably two to four, particularly preferably two to three, very particularly preferably two neutral wash(es) and then separated from the aqueous phase by phase separation; in the case of several washes after each individual wash (step d(iii)). This can in principle be done by all the conventional processes in the state of the art. Preferably completely deionized water (DI water), particularly preferably a mixture of DI water and steam condensate (i.e. a condensate of water vapour which has been obtained by heat exchange from water with any desired exothermic process steps) and very particularly preferably steam condensate is used as washing water here. A procedure in which an electrophoresis is employed in the last neutral wash is preferred (see WO 2012/013678 A2).

The washed nitrobenzene is finally freed from dissolved water, unreacted benzene and any organic impurities by further working up (step d(iv)). This working up is preferably carried out by distillation, the vapours of water and benzene and any organic impurities being expelled overhead. The vapours are cooled and fed into a separating tank. Water settles in the lower phase and is separated off. The upper phase comprises benzene and low-boiling substances, which are fed back again to the reaction as recycled benzene (d.2). A rectification column is preferably employed as the distillation apparatus. The bottom product of the distillation, optionally after a further distillation in which nitrobenzene is obtained as the distillate (i.e. as head or side stream product), is supplied to further applications (such as hydrogenation to form aniline) as pure nitrobenzene (d.1).

It is thus essential to the invention that an oxidizing agent (c.2) is added to the concentrated aqueous phase (c.1) comprising sulfuric acid (circulating sulfuric acid) at least 1 minute, preferably 1 minute to 10 minutes, particularly preferably 3 minutes to 7 minutes before the phase (c.1) comes into contact with the nitric acid stream (a.3), to an extent such that a concentration of oxidizing agent (c.2) of from 10 ppm to 5,000 ppm, preferably 50 ppm to 2,000 ppm and particularly preferably 100 ppm to 1,000 ppm, in each case based on the total weight of the concentrated aqueous phase (c.1) comprising sulfuric acid to be recycled into step a), is established. The minimum period of time of 1 minute is essential, because with a shorter residence time of the nitric acid in the sulfuric acid the positive effects (avoiding of precipitates) no longer arise. For example, it is not sufficient to add the oxidizing agent (c.2) on the suction side of the sulfuric acid circulating pump directly before the nitration reaction, since in this case as a rule it takes less than 30 seconds for the circulating sulfuric acid (c.1) to enter into the nitration reactor. Preferred oxidizing agents are nitric acid (c.2.1), nitrous acid (c.2.2) and/or nitrosylsulfonic acid (c.2.3).

In a preferred embodiment of the process according to the invention, the circulating sulfuric acid (c.1) is held ready in a sulfuric acid reservoir tank for its use in step a), and the addition of the oxidizing agent (c.2), preferably the nitric acid (c.2.1), takes place in the pipeline carrying sulfuric acid between the evaporation apparatus (the so-called "flash evaporator") and the sulfuric acid reservoir tank, preferably with intensive mixing.

If according to the invention an oxidizing agent is added to the circulating sulfuric acid (c.1) before it is recycled into step a) and employed as a constituent of (a.2), the following advantages result for the preparation of nitrobenzene:
  i) Only traces of black precipitate occur in the crude nitrobenzene heat exchanger and in the phase separation apparatus, so that the plant availability is greatly improved.
  ii) Only very slight caking occurs at the exit of the phase separation apparatus to the crude nitrobenzene tank.
  iii) Maintenance costs (cleaning of the apparatuses) are reduced.
  iv) Combustion costs for elimination of residue do not arise.

This procedure according to the invention is also not obvious to the person skilled in the art since he must assume that a treatment of the circulating sulfuric acid after the flash evaporator brings no further positive effect because no black precipitate at all is to be found in the region of the exit of the flash evaporator, in the pipelines to the sulfuric acid reservoir tank and in the sulfuric acid reservoir tank itself.

EXAMPLES

Examples 1 and 2

Preliminary Experiments on Laboratory Scale

Example 1

Solutions of 50 g of circulating sulfuric acid which originate from the sulfuric acid reservoir tank of an adiabatically operated nitrobenzene plant and to which 0.88 g of nitrobenzene were added were temperature-controlled at 150° C. in a closed glass bottle, with shaking, over various lengths of time. When the manual experiments had ended, the particular solutions were filtered through a glass fibre filter having a pore size of 0.6 μm. The filters, including the precipitate, were dried for 21 hours at 55° C. under a pressure of 100 mbar. The black precipitates which remained on the filter were weighed (see Table 1).

TABLE 1

| Dependence of the amount of precipitate on the duration of the temperature control | | | | | | |
|---|---|---|---|---|---|---|
| Period of time [h] | 0 | 12 | 30 | 52 | 76 | 102 |
| Precipitate [g] | 0 | 0.09 | 0.23 | 0.34 | 0.36 | 0.37 |

As expected, the amount of black precipitate increased with the duration of the manual experiment. Elemental analysis for C (carbon), H (hydrogen), N (nitrogen) and O (oxygen) gave a similar result to that for the black precipitate from Example 3 (C, 56.3%; H, 3.0%; N, 4.3%; O, 34.2%; S, 2.0%). An IR analysis showed the presence of amines. Thin layer chromatography in combination with UV detection and chemical detection with pinacryptol yellow indicated sulfonic acid. Thin-layer chromatography in combination with diazotization with N-(1-naphthyl)ethylenediamine dihydrochloride (Bratton-Marshall reagent) confirmed the presence of amines. The two greatest unknowns from the thin layer chromatography could be isolated and identified as aminobenzenesulfonic acid and 4-aminophenol on the basis of their chemical position in the chromatogram by comparison with a databank. The presumption is suggested that the above precipitate could correspond to the black precipitate described in the article "*Researches on the action of sulfuric acid on certain nitrocarbocyclic compounds. I. The action of nitrobenzene*" by M. L. Crossley and C. B. Ogilvie in J. Am. Chem. Soc., 1917, vol. 39 [1], p. 117-122.

Example 2

The experiments were carried out as described under Example 1. The duration of the experiment was in each case 23 hours. Various amounts of different oxidizing agents were added to the solutions. The amount of black precipitate was weighed again. The colour of the solutions and the formation of brown nitrogen oxide gases were analysed qualitatively. The formation of dinitrobenzene in the solutions was analysed quantitatively (see Table 2).

TABLE 2

Influence of the nature and amount of oxidizing agent on the amount of precipitate, evolution of NOx, colour of the solution and dinitrobenzene content of the solution

| Oxidizing agent | Comparison: without oxidizing agent | Nitric acid | | Nitrous acid[a] | | Nitrosylsulfonic acid | |
|---|---|---|---|---|---|---|---|
| Amount [ppm] | 0 | 1,000 | 5,000 | 1,000 | 5,000 | 1,000 | 5,000 |
| Precipitate [g] | 0.2 | 0.05 | 0.01 | 0.15 | 0.02 | 0.02 | 0.01 |
| Colour | black | black | pale yellow | black | pale yellow | black | pale yellow |
| Dinitrobenzene [ppm] | 2 | 175 | 2530 | not determined | 52 | not determined | 10 |
| Nitrogen oxides | no | no | yes | yes | yes | no | no |

[a]Prepared in situ from sodium nitrite.

It can be seen that the formation of black precipitate is greatly reduced by using oxidizing agent. If increased amounts of nitric acid are employed and with nitrous acid, brown nitrogen oxide gases are formed. Increased amounts of dinitrobenzene are formed above all if increased amounts of nitric acid are used as the oxidizing agent. The significant reduction in the precipitate is an advantage which more than compensates the occurrence of nitrogen oxide gases and the formation of dinitrobenzene.

Examples 3 to 7

Comparison of the Procedure According to the Invention with the Procedure of the State of the Art Under Operating Conditions General Conditions for the Preparation of Nitrobenzene A stream of sulfuric acid into which first a stream of nitric acid and then a combined stream of fresh benzene and recycled benzene were metered is fed to a reactor. The residence time between the addition of nitric acid to the sulfuric acid and the entry of the nitrating solution into the reactor is less than 10 seconds. 6% of recycled benzene are used as excess benzene. After complete reaction of the nitric acid with the benzene to give nitrobenzene under an adiabatic reaction procedure, the now approx. 130° C. hot reaction product is fed to a phase separation apparatus in which the reaction product breaks down into an organic phase (=crude nitrobenzene, also comprising benzene in addition to nitrobenzene) and an aqueous phase (=waste acid, also comprising small contents of nitrobenzene and benzene in addition to sulfuric acid). The aqueous phase mainly encompassing sulfuric acid is subjected to a flash evaporation of water in an evaporator by sudden pressure reduction and is concentrated in this manner. The concentrated sulfuric acid is temporarily stored in a sulfuric acid reservoir tank to be used again in the nitration. After the crude nitrobenzene has been separated off in the phase separation apparatus, it is cooled to approx. 40° C. to 50° C. in a crude nitrobenzene cooler and fed to a wash for work-up. The purified nitrobenzene stream thus obtained, which has been largely freed from nitrophenols and salts is reheated and freed from water and benzene, which are separated off overhead, in a rectification column, as a result of which dried pure nitrobenzene is obtained in the bottom of the column. The condensed head product of the rectification column is fed to a phase separation apparatus in which the head product breaks down into an organic phase (comprising benzene) and an aqueous phase. The benzene is stored temporarily in a buffer tank and from there is returned as recycle benzene into the inlet of the reactor for reaction, as already described above.

Example 3

Comparative Example

The preparation of nitrobenzene was carried out as described in the general conditions for the preparation of nitrobenzene. Black, suspended particles of solid collected in the phase separation layer in the phase separation apparatus, and at the exit of the separation apparatus to the crude nitrobenzene tank there was black caking, which had to be removed from the apparatus twice a year in order to avoid operating malfunctions. The heat exchanger for the crude nitrobenzene cooling downstream of the phase separation apparatus had to be opened ten times a year in order to remove black precipitate which prevented the crude nitrobenzene from draining off.

TABLE 3

Analysis of the black precipitate:

| Element | C | H | N | O | S | Si | Metals |
|---|---|---|---|---|---|---|---|
| Amount[a] (%) | 58.5 | 3.6 | 4.2 | 31.5 | 1.3 | 0.7 | 0.2 |

TABLE 4

Metals detected in the black precipitate:

| Metal | Al | Cr | Cu | Fe | Pd | Pt | Ta | Ti |
|---|---|---|---|---|---|---|---|---|
| Amount[a] (%) | 0.010 | 0.029 | 0.006 | 0.011 | 0.059 | 0.063 | 0.007 | 0.008 |

[a]Content by weight, based on the weight of the black precipitate.

C (carbon), H (hydrogen), N (nitrogen) and O (oxygen) were determined by elemental analysis. Si (silicon), S (sulfur) and metals were determined by x-ray fluorescence.

Example 4

Comparative Example

The preparation of nitrobenzene was carried out as described in the general conditions for the preparation of nitrobenzene with the following additional measures:

500 ppm of nitric acid were added on the suction side of the sulfuric acid circulation pump in order to render passive the pump. The sulfuric acid treated in this way had a residence time of approx. 3 seconds until entry into the reaction. Between the sulfuric acid pump and the inlet of the reactor, first nitric acid and then, directly at the reactor inlet, benzene were metered into the sulfuric acid stream. The problems with the black precipitate were exactly as described in Example 1. Analysis exhibited a chemically identical composition as that in Example 1 within the limits of measurement accuracy.

Example 5

According to the Invention

The preparation of nitrobenzene was carried out as described in the general conditions for the preparation of nitrobenzene with the exception of the following additional measures:

Nitric acid (c.2.1) was passed continuously into the sulfuric acid reservoir tank such that a calculated weight content of nitric acid, based on the total weight of sulfuric acid and nitric acid, of 1,000 ppm was established. The sulfuric acid (c.1) treated in this way had a residence time of approx. 5 min until entry into the nitration reaction (step a)). Only traces of black precipitate were observed through an inspection glass in the phase separation apparatus. The heat exchanger for the crude nitrobenzene cooling downstream of the phase separation apparatus had to be opened only once a year in order to remove black precipitate which prevents the crude nitrobenzene from draining off.

Example 6

According to the Invention

The preparation of nitrobenzene was carried out as described in the general conditions for the preparation of nitrobenzene with the following additional measures:

Nitric acid (c.2.1) was passed continuously into the sulfuric acid reservoir tank such that a calculated weight content of nitric acid, based on the total weight of sulfuric acid and nitric acid, of 200 ppm was established. The sulfuric acid (c.1) treated in this way had a residence time of approx. 5 min until entry into the nitration reaction (step a)). Only traces of black precipitate were observed through an inspection glass in the phase separation apparatus. The heat exchanger for the crude nitrobenzene cooling downstream of the phase separation apparatus had to be opened only once a year in order to remove black precipitate which prevents the crude nitrobenzene from draining off.

Example 7

According to the Invention

The preparation of nitrobenzene was carried out as described in the general conditions for the preparation of nitrobenzene with the following additional measures:

Nitrosylsulfonic acid (c.2.3) was passed continuously into the sulfuric acid reservoir tank such that a calculated weight content of nitrosylsulfonic acid, based on the total weight of sulfuric acid and nitric acid, of 40 ppm was established. Only traces of black precipitate were observed through an inspection glass in the phase separation apparatus. The heat exchanger for the crude nitrobenzene cooling downstream of the phase separation apparatus had to be opened only once a year in order to remove black precipitate which prevents the crude nitrobenzene from draining off.

The invention claimed is:

1. A continuously operated adiabatic process for the preparation of nitrobenzene by nitration of benzene, comprising:
   a) reacting a benzene-containing stream (a.1) in a reactor with sulfuric acid (a.2) and nitric acid (a.3) under adiabatic conditions, wherein benzene is employed in a stoichiometric excess, based on nitric acid (a.3),
   b) separating the process product obtained in step a) in a phase separation apparatus into an aqueous phase (b.1) comprising sulfuric acid and an organic phase (b.2) comprising nitrobenzene,
   c) concentrating the aqueous phase (b.1) obtained in step b) by evaporation of water to give an aqueous phase (c.1) having an increased sulfuric acid concentration compared with (b.1), wherein phase (c.1) is returned into step a) and is used as a component of (a.2), and
   d) working up the organic phase (b.2) obtained in step b) to give pure nitrobenzene (d.1),
   wherein
   an oxidizing agent (c.2) is added to the concentrated aqueous phase (c.1) comprising sulfuric acid at least 1 minute before the phase (c.1) comes into contact with the nitric acid stream (a.3), to an extent such that a concentration of the oxidizing agent (c.2) of from 10 ppm to 5,000 ppm, based on the total weight of the concentrated aqueous phase (c.1) comprising sulfuric acid to be returned into step a), is established.

2. The process of claim 1, wherein the oxidizing agent (c.2) is selected from the group consisting of nitric acid (c.2.1), nitrous acid (c.2.2), nitrosylsulfonic acid (c.2.3) and a mixture of at least two of these oxidizing agents.

3. The Process of claim 2, wherein the oxidizing agent (c.2) is added 1 minute to 10 minutes before the phase (c.1) comprising sulfuric acid comes into contact with the nitric acid stream (a.3).

4. The process of claim 2, wherein the oxidizing agent (c.2) is added 3 minutes to 7 minutes before the phase (c.1) comprising sulfuric acid comes into contact with the nitric acid stream (a.3).

5. The process of claim 1, wherein a concentration of the oxidizing agent (c.2) of from 50 ppm to 2,000 ppm, based on the total weight of the concentrated aqueous phase (c.1) comprising sulfuric acid to be recycled into step a), is established.

6. The process of claim 1, wherein a concentration of the oxidizing agent (c.2) of from 100 ppm to 1,000 ppm, based on the total weight of the concentrated aqueous phase (c.1) comprising sulfuric acid to be recycled into step a), is established.

7. The process of claim 1, wherein the phase (c.1) comprising sulfuric acid is held ready in a sulfuric acid reservoir tank for its use in step a), and in which the addition of the oxidizing agent (c.2) takes place in a pipeline from the evaporation apparatus employed in step c) to the sulfuric acid reservoir tank.

* * * * *